US012734079B2

(12) United States Patent
Wang et al.

(10) Patent No.: US 12,734,079 B2
(45) Date of Patent: Sep. 15, 2026

(54) PATTERNED APERTURED NONWOVEN

(71) Applicant: The Procter & Gamble Company, Cincinnati, OH (US)

(72) Inventors: Sijia Wang, Beijing (CN); Fancheng Wang, Beijing (CN); Yuhan Wang, Beijing (CN); Meng Chen, Beijing (CN); Xiaoxin Liu, Beijing (CN)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 255 days.

(21) Appl. No.: 18/635,141

(22) Filed: Apr. 15, 2024

(65) Prior Publication Data

US 2024/0252369 A1 Aug. 1, 2024

Related U.S. Application Data

(63) Continuation of application No. 17/510,700, filed on Oct. 26, 2021, now Pat. No. 12,004,933.

(30) Foreign Application Priority Data

Oct. 30, 2020 (WO) ................ PCT/CN2020/125247

(51) Int. Cl.
*A61F 13/514* (2006.01)
*A61F 13/15* (2006.01)

(52) U.S. Cl.
CPC .... *A61F 13/5146* (2013.01); *A61F 13/15707* (2013.01); *A61F 13/51401* (2013.01);
(Continued)

(58) Field of Classification Search
CPC .......... A61F 13/15707; A61F 13/51401; A61F 2013/51443; A61F 2013/51452; A61F 2013/5127; A61F 13/512; A61F 13/5146
See application file for complete search history.

(56) References Cited

U.S. PATENT DOCUMENTS 5,817,394 A 10/1998 Alikhan et al.
D508,613 S 8/2005 Knobloch et al.
(Continued)

FOREIGN PATENT DOCUMENTS

CN 2331362 Y 8/1999
EP 4062884 A1 9/2022
(Continued)

OTHER PUBLICATIONS

PCT Suppl. Search Report and Written Opinion for PCT/CN2020/125247 dated Feb. 6, 2023, 11 pages.
(Continued)

*Primary Examiner* — Susan S Su
(74) *Attorney, Agent, or Firm* — Sarah M. DeCristofaro

(57) ABSTRACT

The present disclosure relates to a nonwoven substrate comprising a plurality of apertures that form a pattern and define a plurality of discrete non-aperture zones. Each of the plurality of discrete non-aperture zones has a periphery formed by a continuous line of apertures, with adjacent apertures being spaced apart by an edge-to-edge distance of no more than 3 mm, while each of the plurality of discrete non-aperture zones is substantially free of apertures within the periphery. Particularly, the area ratio of such plurality of discrete non-aperture zones over the nonwoven substrate ranges from 60% to 90%, and at least some of said plurality of discrete non-aperture zones have an area of 100 $mm^2$ or more.

20 Claims, 10 Drawing Sheets

(52) U.S. Cl.
CPC ............... *A61F 2013/51443* (2013.01); *A61F 2013/51452* (2013.01)

(56) References Cited

U.S. PATENT DOCUMENTS

| | | | | |
|---|---|---|---|---|
| D720,544 | S | 1/2015 | Seitzinger et al. | |
| D738,632 | S | 9/2015 | Seitzinger et al. | |
| 2004/0253892 | A1 | 12/2004 | Baker et al. | |
| 2005/0228353 | A1* | 10/2005 | Thomas | B29C 59/06 604/383 |
| 2014/0324009 | A1 | 10/2014 | Lee | |
| 2016/0129663 | A1 | 5/2016 | Moss | |
| 2016/0136014 | A1 | 5/2016 | Arora | |
| 2018/0214321 | A1 | 8/2018 | Ashraf | |
| 2018/0229216 | A1 | 8/2018 | Smith et al. | |
| 2022/0133551 | A1 | 5/2022 | Wang et al. | |
| 2024/0183083 | A1 | 6/2024 | Ashraf | |

FOREIGN PATENT DOCUMENTS

| | | | |
|---|---|---|---|
| JP | 5203349 | B2 | 7/2011 |
| WO | 2016073712 | A1 | 5/2016 |
| WO | 2016103774 | A1 | 6/2016 |
| WO | 2020210995 | A1 | 10/2020 |
| WO | 2021163869 | A1 | 8/2021 |

OTHER PUBLICATIONS

PCT Search Report and Written Opinion for PCT/CN2020/125247 dated Jul. 30, 2021,10 pages.
All Office Actions; U.S. Appl. No. 17/510,700, filed Oct. 26, 2021.

* cited by examiner

PATTERNED APERTURED NONWOVEN

CROSS REFERENCE TO RELATED APPLICATIONS

This application is a continuation of, and claims priority under 35 U.S.C. § 120 to, U.S. patent application Ser. No. 17/510,700 filed on Oct. 26, 2021, which claims the benefit, under 35 USC 119(e), to PCT Application No. PCT/CN2020/125247 filed on Oct. 30, 2020, which are herein incorporated by reference in their entirety.

FIELD OF THE INVENTION

The present invention relates to nonwoven having patterns thereon that are formed by apertures, as well as absorbent article comprising the same and a method for manufacturing the same.

BACKGROUND OF THE INVENTION

Absorbent articles have been used as personal hygiene products, such as sanitary napkins, infant disposable diapers, training pants for toddlers, adult incontinence undergarments, and the like. Such absorbent articles are designed to absorb and contain body exudates, in particularly large quantities of urine, runny BM, and/or menses (together the "fluids"). These absorbent articles may comprise several layers providing different functions, for example, a topsheet, a backsheet, and an absorbent core disposed therebetween, among other layers (e.g., acquisition layer, distribution layer, etc.) as desired.

The topsheet is generally liquid permeable and is configured to receive the fluids being excreted from the body and aid in directing the fluids toward an acquisition system, a distribution system, and/or the absorbent core. One design criterion of topsheets is to reduce the amount of time the fluids spend on such topsheet prior to being absorbed by the absorbent article. If fluids remain on the surface of a topsheet for too long of a period of time, the wearer may not feel dry and skin discomfort may increase.

To solve the problem of the skin feeling wet during or shortly after, for example, urination, because of prolonged fluid residency on the topsheets, apertured nonwoven webs made from synthetic fibers have been to form topsheets. Such apertured nonwovens contain a plurality of apertures extending from a top surface therethrough to a bottom surface, which allows speedy drainage of the fluids away from the topsheet into the underlying acquisition system and thereby reduces ponding of the fluids on the topsheet before they are absorbed by the absorbent article.

Further, apertured nonwovens can also be used to form the outermost layer of the backsheet of such absorbent article to improve the overall breathable appearance of such absorbent article and delight the consumer.

There is a continuing need for apertured nonwovens to have patterns that are overall more visually appealing to and preferred by the consumers. Particularly, it is advantageous to provide patterned and apertured nonwovens that may convey to the consumers an improved sense of premiumness. It is also advantageous to provide patterned and apertured nonwovens that may convey to the consumers an improved sense of breathability, softness, absorbency, distinctiveness, and/or three-dimensionness (3Dness).

SUMMARY OF THE INVENTION

The present invention provides a nonwoven substrate comprising: (a) a top surface; (b) a bottom surface; and (c) a plurality of apertures, each of which extends from the top surface through said nonwoven substrate to the bottom surface, while the plurality of apertures define a plurality of discrete non-aperture zones. Each of the plurality of discrete non-aperture zones has a periphery formed by a continuous line of apertures, with adjacent apertures being spaced apart by an edge-to-edge distance of no more than 3 mm. Further, each of the plurality of discrete non-aperture zones is substantially free of apertures within the periphery. The area ratio of such plurality of discrete non-aperture zones over the nonwoven substrate ranges from about 60% to about 90%, or from about 62% to about 80%, or from about 65% to about 75%. At least some of said plurality of discrete non-aperture zones are sufficiently large, i.e., having an area of about 100 $mm^2$ or more, or about 150 $mm^2$ or more.

It is a surprising and unexpected discovery of the present invention that the apertured nonwoven substrate as described hereinabove is more appealing to the consumers (i.e., with a better overall liking or OAR scare) and/or is more likely to convey to the consumers an improved sense of premiumness. The apertured nonwoven substrate of the invention may further provide the consumers with an improved sense of breathability, softness, absorbency, distinctiveness, and/or 3Dness.

In a preferred embodiment of the present invention, each of the plurality of apertures has a size ranging from 0.2 $mm^2$ to 1.5 $mm^2$, or from 0.4 $mm^2$ to 1.3 $mm^2$, and/or a diameter ranging from 0.5 mm to 1.5 mm, or from 0.7 mm to 1.2 mm. The plurality of apertures may have regular shapes selected from the group consisting of circle, oval, triangle, square, rectangle, parallelogram, trapezoid, polygon, hourglass, star, and any combinations thereof.

In a preferred embodiment of the present invention, each of the plurality of discrete non-aperture zones has an area of more than 6 $mm^2$, and/or a minor dimension of more than 2.5 mm. More preferably, some of said plurality of discrete non-aperture zones have a major dimension of 15 mm or more.

Further, it is preferred that the plurality of apertures further define one or more aperture zones, each of which comprises four or more apertures therein, while each aperture within each of said aperture zones has at least three adjacent apertures that are spaced apart from it by an edge-to-edge distance of no more than 3 mm. The nonwoven substrate of the present invention may comprise a plurality of discrete aperture zones, or it may comprise a continuous aperture zone.

In a particularly preferred embodiment of the present invention, the nonwoven substrate is a relofted nonwoven. Further, the nonwoven substrate may have a compression work no less than about 700 gf×mm, as measured according to Compression Property Test; and/or a basis weight in the range of about 15 gsm to about 75 gsm.

The present invention also provides an absorbent article comprising a liquid pervious topsheet, a liquid impervious backsheet, an absorbent structure disposed between the topsheet and the backsheet, while either the liquid pervious topsheet or the liquid impervious backsheet comprises the above-described apertured nonwoven substrate.

The present invention also provides a method for manufacturing the above-described apertured nonwoven substrate, comprising the steps of: providing a nonwoven substrate having a top surfaced and a bottom surface; and forming a plurality of apertures that each extends from the top surface through said nonwoven substrate to the bottom surface, wherein said plurality of apertures define a plurality of discrete non-aperture zones; wherein each of said plurality of discrete non-aperture zones has a periphery formed by a continuous line of apertures, with adjacent apertures being spaced apart by an edge-to-edge distance of no more than 3 mm; wherein each of said plurality of discrete non-aperture zones is substantially free of apertures within the periphery; and wherein the area ratio of said plurality of discrete non-aperture zones over said nonwoven substrate ranges from 60% to 90%.

These and other features, aspects, and advantages of the present invention will become evident to those skilled in the art from a reading of the present disclosure.

DETAILED DESCRIPTION OF THE INVENTION

Figure 1A:
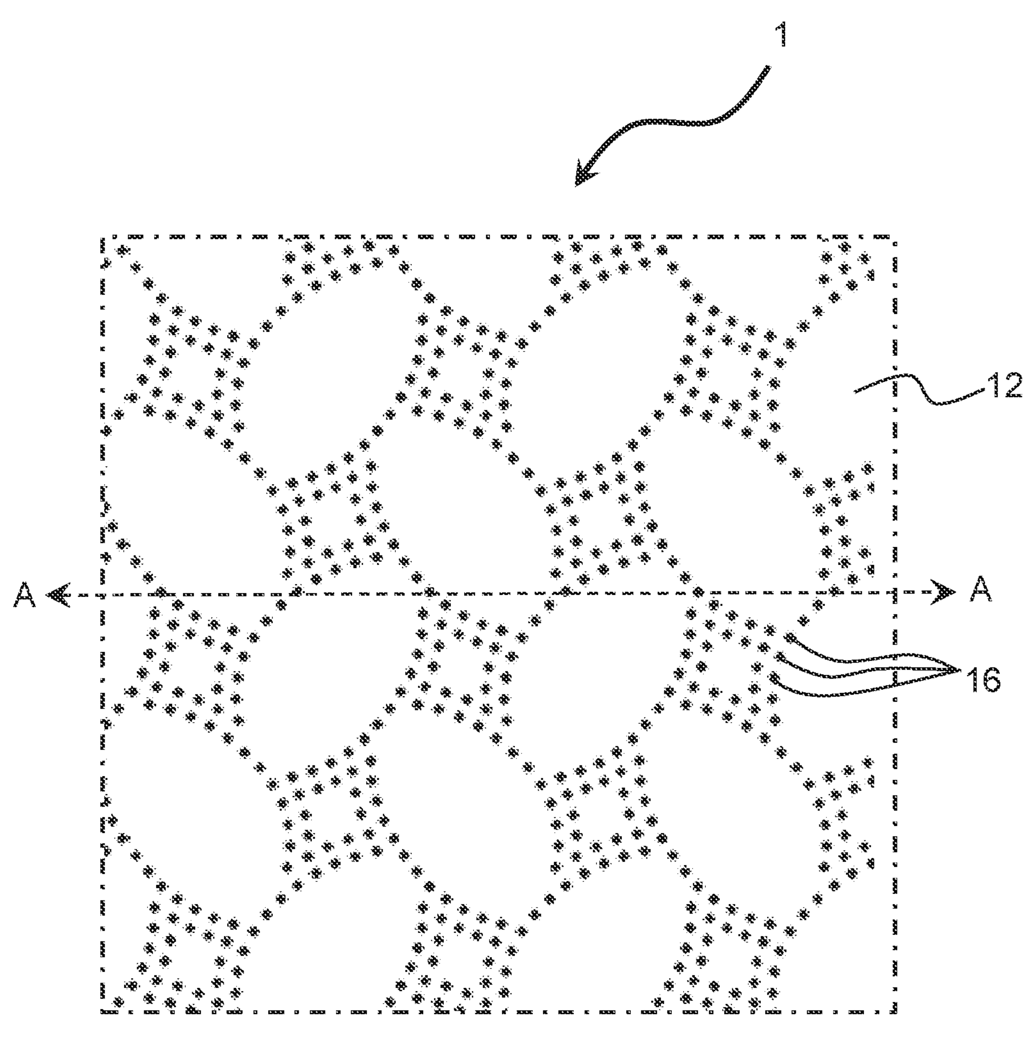
FIG. 1A is a top schematic view of an apertured nonwoven substrate with a specific pattern formed by a plurality of apertures, according to one embodiment of the present invention.

All ranges are inclusive and combinable. The number of significant digits conveys neither limitations on the indicated amounts nor on the accuracy of the measurements. All numerical amounts are understood to be modified by the word "about" unless otherwise specifically indicated.

The term "absorbent articles", as used herein, include disposable diapers, sanitary napkins, panty liners, incontinence pads, interlabial pads, breast-milk pads, sweat sheets, animal-use excreta handling articles, animal-use diapers, and the like.

The term "component" of an absorbent article, as used herein, refers to an individual constituent of an absorbent article, such as a topsheet, secondary layer, acquisition layer, liquid handling layer, absorbent core or layers of absorbent cores, and backsheets.

The term "discrete" refers to a zone or area that has a clearly defined periphery that is not connected with or overlapping with any other zone or area of the same category (i.e., aperture zones vs. non-aperture zones) in any substantial manner (i.e., if there are some overlaps, the overlapping portion is no more than 50%, or no more than 40%, or no more than 30%, of its overall periphery).

The term "non-aperture zone" or "non-aperture zones" refers to the smallest zone or area that is enclosed by a periphery defined by a continuous line of apertures, with adjacent apertures being spaced apart by an edge-to-edge distance of no more than 3 mm, while such zone or area is substantially free of apertures within such periphery.

The term "substantially free of apertures" refers to a discrete non-aperture zone containing few or no apertures within its periphery (i.e., if present, the number of apertures within its peripheral is less than about 10%, or less than about 5%, or less than about 1% of the total number of apertures along its periphery).

The term "aperture zone" or "aperture zones" refers to the zone or area that encompasses a cluster of four or more apertures, wherein each aperture in said cluster has at least three adjacent apertures that are spaced apart from by an edge-to-edge space (i.e., the shortest space between an edge of one aperture to an edge of an adjacent aperture, which is referred to hereinafter as "ED") of no more than about 3 mm.

The term "major dimension" refers to the greatest dimension of a discrete zone or area measured from one extreme side to the other extreme side.

The term "minor dimension" refers to a second dimension of said discrete zone or area measured also from one extreme side to the other extreme side but along a direction perpendicular to the above-mentioned major dimension.

Nonwoven Substrate

The present invention provides a nonwoven substrate suitable for a component of an absorbent article.

As used herein, the term "nonwoven" or "nonwoven substrate" refers to a web having a structure of individual fibers or threads which are interlaid, but not in a repeating pattern as in a woven or knitted fabric, which do not typically have randomly oriented fibers. Nonwoven substrates or fabrics have been formed from many processes, such as, for example, meltblowing, spunbonding, hydroentangling, airlaid, wetlaid, through-air-dried paper making processes, and bonded carded web processes, including carded thermal bonding. The nonwoven substrates can comprise unbonded fibers, entangled fibers, tow fibers, or the like. Fibers can be extensible and/or elastic, and may be pre-stretched for processing. Fibers can be continuous, such as those produced by spunbonded methods, or cut to length, such as those typically utilized in a carded process. Fibers can be bicomponent, multiconstituent, shaped, crimped, or in any other formulation or configuration known in the art for nonwoven substrates and fibers. In general, the fibers can be bondable, either by chemical bond (e.g. by latex or adhesive bonding), pressure bonding, or thermal bonding. If thermal bonding techniques are used in the bonding process described below, a certain percentage of thermoplastic material, such as thermoplastic powder or fibers can be used.

The nonwoven of the present invention has an appropriate amount of cushioning and bulkiness recovery characteristics.

As such, the nonwoven of the present invention can be used in applications in which the nonwoven is in contact with the skin, specifically applications in which the first web layer is the surface that is in contact with the skin. The nonwoven of the present invention can be used as a topsheet for an absorbent article in which the surface of first web layer is in contact with the skin.

The nonwoven substrate of the present invention may meet certain parametric requirements as detailed below. Among the parameters of interest, Compression Work (CW) is obtained from the FTT Test under Compression Property Test below. Information about the FTT Test method may be found in the paper "Fibers and Polymers 2014, Vol. 15, No. 7, 1548-1559" titled "A Simultaneous Measurement Method to Characterize Touch Properties of Textile Materials" by Xiao Liao et al.

The nonwoven substrate may have a compression work no less than about 700 gf×mm, or no less than about 800 gf×mm, or no less than about 900 gf×mm as measured according to Compression Properties described under the TEST METHODS. Compression work is a parameter which can indicate compliance property of a specimen by quantifying the total work done on the specimen during the compression process. A higher compression work in nonwoven may represent a more cushiony property which drives desired consumer benefits of a softness perception as well as comfortable usage experience. Without wishing to be bound by theory, it is believed that the nonwoven substrate of the present invention may exhibit high compression work due to a lofted and airy structure in the non-aperture zones.

The nonwoven substrate of the present invention may be a relofted nonwoven. Relofting process is a process which provide heat or energy a nonwoven web so that the nonwoven web regain its bulkiness.

The nonwoven substrate of the present invention may comprise one or more layers.

In some embodiments, the nonwoven substrate comprises at least two layers each of which remains as a discrete layer which may be attached to each other by, for example, thermal bonding, compression, adhesive bonding or any combination thereof. The first layer and the second layer in the nonwoven substrate may be bonded to each other without using chemicals such as adhesive and latex.

In some embodiments, the nonwoven substrate comprises a unitary structure. A unitary structure herein intends to mean that although it may be formed by several sub-layers that have distinct properties and/or compositions from one another, they are somehow intermixed at the boundary region, so that, instead of a definite boundary between sub-layers, it would be possible to identify a region where the different sub-layers transition one into the other. Such a unitary structure is typically built by forming the various sub-layers one on top of the other in a continuous manner, for example using air laid or wet laid deposition. Typically, there is no adhesive used between the sub-layers of the unitary material. However, in some cases, adhesives and/or binders can be present although typically in a lower amount that in multilayer materials formed by separate layers.

The nonwoven substrate may comprise thermoplastic fibers. The nonwoven substrate may comprise any suitable types of thermoplastic fibers, such as polypropylene fibers, other polyolefins, other polyesters besides PET such as polylactic acid, thermoplastic starch-containing sustainable resins, other sustainable resins, bio-PE, bio-PP, and Bio-PET. The nonwoven substrate may comprise any other suitable types of fibers such as viscose fibers, rayon fibers, or other suitable nonwoven fibers, for example. These fibers may have any suitable deniers or denier ranges and/or fiber lengths or fiber length ranges.

The nonwoven substrate may comprise bicomponent fibers. Bicomponent fibers can have a sheath and a core. The sheath and the core may also comprise any other suitable materials known to those of skill in the art. The core/sheath composite fibers may comprise a core component comprising a resin and a sheath component comprising a thermoplastic resin having a melting point of at least about 20° C. lower than a melting point of the resin of the core component. The sheath and the core may each comprise about 50% of the fibers by weight of the fibers, although other variations (e.g., sheath 60%, core 40%; sheath 30%, core 70% etc.) are also within the scope of the present disclosure. The bicomponent fibers or other fibers that make up the first and/or second layers may have a denier in the range of about 0.5 to about 6, about 0.75 to about 4, about 1.0 to about 4, about 1.5 to about 4, about 1.5 to about 3, about 1.5 to about 2.5, or about 2, specifically including all 0.1 denier increments within the specified ranges and all ranges formed therein or thereby. Denier is defined as the mass in grams per 9000 meters of a fiber length. In other instances, the denier of the fibers of the first layer may be in the range of about 1.5 denier to about 6 denier or about 2 denier to about 4 denier and the denier of the fibers of the second layer may be in the range of about 1.2 denier to about 3 denier or about 1.5 denier to about 3 denier, specifically reciting all 0.1 denier increments within the specified ranges and all ranges formed therein or thereby. Bicomponent fibers can be a side-by-side type fibers.

In a form, the basis weight of the nonwoven substrate may be appropriately selected depending on the nonwoven application. For the nonwoven of the present invention as a topsheet of an absorbent article, a basis weight of the nonwoven substrate may be from about 15 gsm (g/m$^2$) to about 75 gsm, or from about 20 gsm to about 75 gsm, or from about 30 gsm to about 65 gsm. All other suitable basis weight ranges for the nonwoven substrate are within the scope of the present disclosure. Accordingly, the basis weight of the nonwoven substrate may be designed for specific product requirements.

Apertures

The nonwoven substrate according to the present invention comprises a plurality of apertures that form a three-dimensional and visually distinctive pattern that conveys a desired sense of premiumness to the consumer.

Figure 1B:
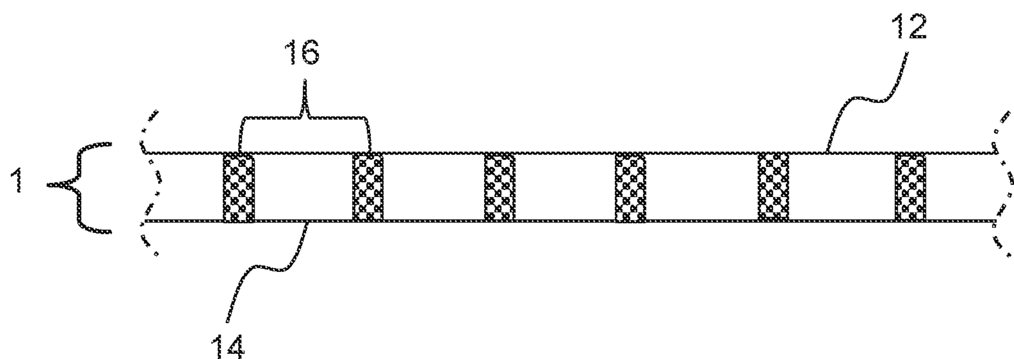
FIG. 1B is a cross-sectional schematic view of the apertured nonwoven substrate of FIG. 1 along Line A-A.

Referring to FIGS. 1A and 1B, an exemplary nonwoven substrate 1 according to the present invention comprises a top surface 12, a bottom surface 14, and a plurality of apertures 16 that each extend from the top surface 12 through the nonwoven substrate 1 to the bottom surface 14.

The plurality of apertures in the nonwoven substrate of the present invention are formed by pin-hole aperturing, punch aperturing, and water-jet aperturing. Typically, the fibers in peripheries of apertures are compressed and heat-fused in comparison with fibers in areas that are free of apertures.

The apertures may be of any regular or irregular shapes. The apertures may have regular shapes selected from the group consisting of circle, oval, triangle, square, rectangle, parallelogram, trapezoid, polygon, hourglass, star, and the like, and any combinations thereof. Polygonal shapes include, but are not limited to pentagonal, hexagonal, and octagonal. In one embodiment, the apertures of the present invention are circular. In another embodiment, the apertures of the present invention are oval.

The size of the above-mentioned apertures is important in achieving the desired fluid encapsulation performance. If the apertures are too small, the fluids may not pass through the apertures, either due to poor alignment of the fluid source and the aperture location or due to runny fecal masses, for example, having a diameter greater than the apertures. If the apertures are too large, the area of skin that may be contaminated by "rewet" from the article is increased. Typically, apertures of the present invention may each have a size (i.e., the area) in a range of from about 0.2 $mm^2$ to about 1.5 $mm^2$, or from about 0.4 $mm^2$ to about 1.3 $mm^2$. Further, apertures of the present invention may each have a diameter (i.e., the major dimension) in a range of from about 0.5 mm to about 1.5 mm, or from about 0.7 mm to about 1.2 mm. When apertures of the present invention have sizes and diameters within the preferred ranges, the patterns formed by such apertures may convey to the consumer an improved sense of premiumness.

The apertures may have the same size and/or shape, but they may have different sizes and/or shapes.

Further, it is discovered by the present invention that the density of apertures (i.e., how close the apertures are placed from each other) may also impact the consumer perception of premiumness. When the overall pattern is the same or similar (i.e., with approximately the same or similar sizes of aperture zones and discrete non-aperture zones arranged in similar spacing from each other), nonwoven substrates with a higher aperture density may convey an improved sense of premiumness to the consumers than those with a lower aperture density.

The apertures of the present invention form a three-dimensional and visually distinctive pattern on the nonwoven substrate. A pattern formed by the apertures may be of any shape, for example, one or multiple linear lines or curved lines, circles, ellipses, triangles, polygons, flowers, clouds, and the like. The pattern formed by the apertures may be regular, homogeneous and uniform, or it may be irregular, non-uniform and/or non-homogeneous. The pattern formed by the apertures may be continuous, or it may be discontinuous. The aperture pattern may coordinate with graphics, indicia, printing, inks, color, and/or patterned adhesives, for example, located in the nonwoven substrate or in another component of the absorbent article when it is used as a component of an absorbent article.

Discrete Non-Aperture Zones

The pattern formed by the apertures according to the present invention define a plurality of discrete non-aperture zones, each of which is the smallest zone or area enclosed by a periphery defined by a continuous line of apertures, with adjacent apertures being spaced apart by an edge-to-edge distance of no more than about 3 mm. The discrete non-aperture zones of the present invention may have any regular or irregular shapes. The discrete non-aperture zones may have regular shapes, such as circles, ellipses, triangles, polygons, leaves, flowers, clouds, and the like. The plurality of discrete non-aperture zones of the present invention may have the same size and/or shape, but they may have different sizes and/or shapes.

A key feature of the present invention is that the area ratio of said plurality of discrete non-aperture zones over said nonwoven substrate, i.e., the total areas of the discrete non-aperture zones divided by the total area of the nonwoven substrate (as measured from a 55 mm×55 mm sample of such nonwoven substrate), ranges from 60% to 90%, or from 62% to 80%, or from 65% to 75%. It is a surprising and unexpected discovery that when the area ratio of the plurality of discrete non-aperture zones over the nonwoven substrate falls within the above range of the present disclosure, the consumers are likely to view the nonwovens as more premium and/or overall more appealing. If the area ratio falls either below 60% or above 90%, the consumers tend to view the nonwovens as less premium or overall unappealing.

Figure 2:
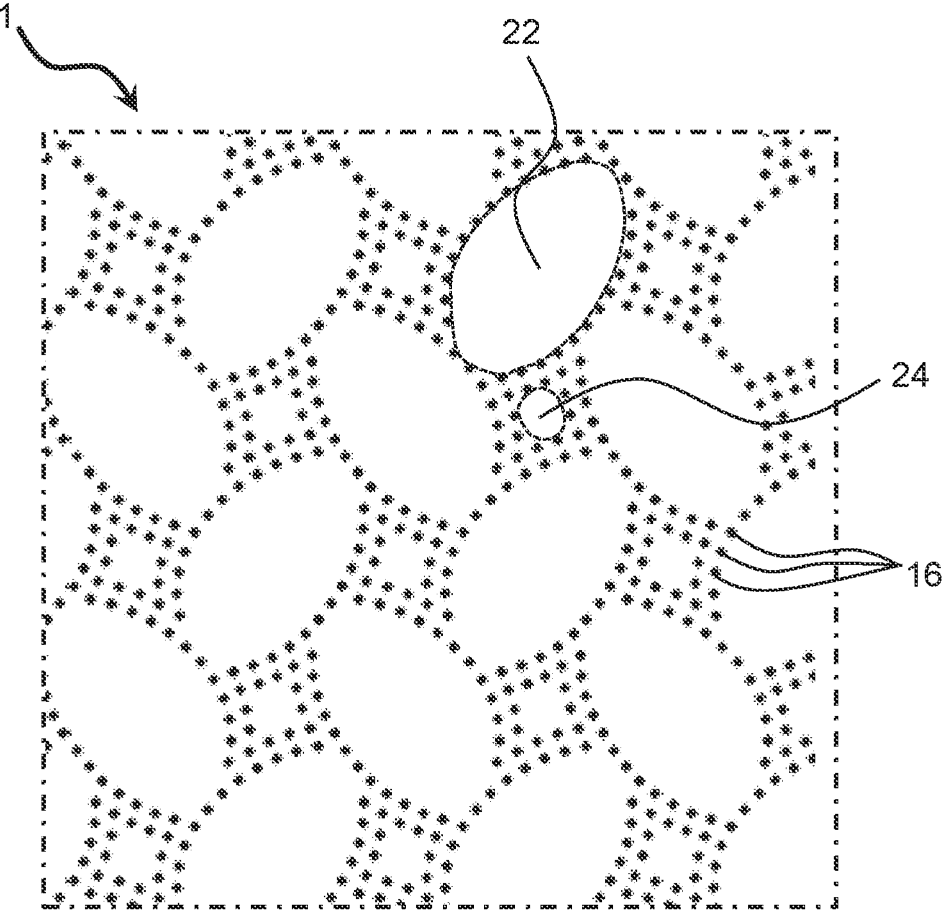
FIG. 2 is the top schematic view of the apertured nonwoven substrate of FIG. 1, with markings showing a plurality of discrete non-aperture zones thereon.

As shown in FIG. 2, the apertures 16 in the nonwoven substrate 1 define a first group of larger leaf-shaped discrete non-aperture zones 22 and a second group of smaller circular discrete non-aperture zones 24, while each of the zones 22 and 24 are free of apertures within their respective peripheries (as marked by the dotted lines). The area ratio of the non-aperture zones 22 and 24 over the nonwoven substrate 1 (as measured from a 55 mm×55 mm sample of such nonwoven substrate) is about 75%.

Figure 3A:
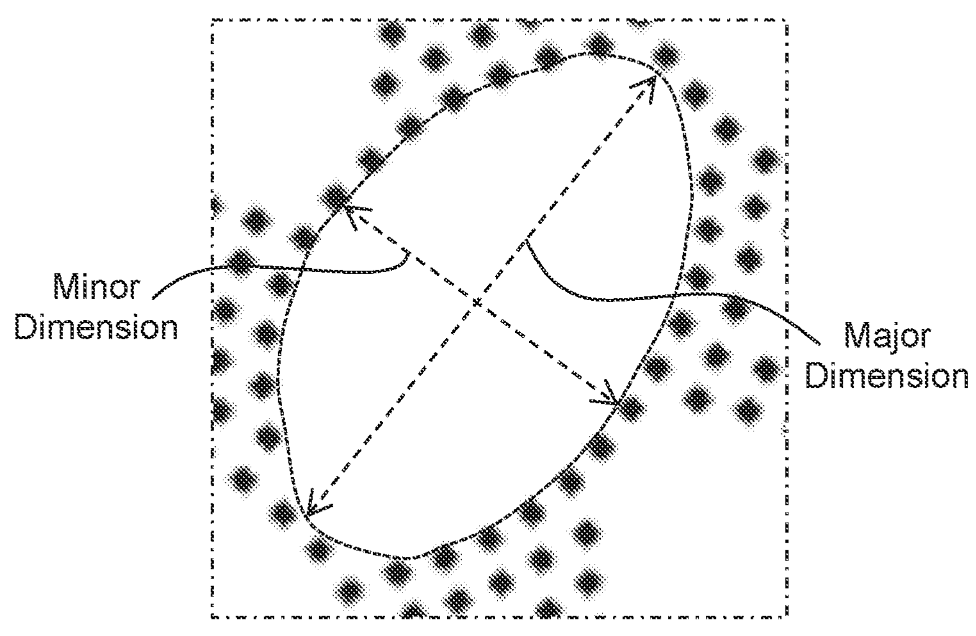
FIG. 3A is an enlarged schematic view of one discrete non-aperture zone on the apertured nonwoven substrate of FIG. 1.

Each of the discrete non-aperture zones has a major dimension and a minor dimension. For example, FIG. 3A shows the major and minor dimensions of the leaf-shaped discrete non-aperture zones 22 on the nonwoven substrate 2.

Each of the discrete non-aperture zones of the present invention may have an area of more than about 6 $mm^2$, or about 8 $mm^2$ or more, or about 10 $mm^2$ or more, or about 15 $mm^2$ or more. The minor dimension of each of the discrete non-aperture zones can be more than about 2.5 mm, or about 3 mm or more, or about 4 mm or more, or about 5 mm or more.

It is particularly preferred that at least some of the discrete non-aperture zones (i.e., "major discrete non-aperture zones") of the present invention have a relatively large size, e.g., the larger leaf-shaped discrete non-aperture zones 22 as shown in FIG. 2. Such major discrete non-aperture zones may have an area of about 100 $mm^2$ or more, or about 150 $mm^2$ or more, or about 200 $mm^2$ or more, or about 300 $mm^2$ or more. Further, such major discrete non-aperture zones may have a major dimension of about 15 mm or more, or about 18 mm or more, or about 20 mm or more. When the major discrete non-aperture zones of the present invention have the preferred areas and/or major dimensions, the patterns formed by such apertures may be better liked by the consumers (i.e., with a better overall liking rate or OAR score) and/or may convey to the consumer an improved sense of premiumness. For example, the larger leaf-shaped discrete non-aperture zones 22 as shown in FIG. 2 each has an area of about 189 $mm^2$ and a major dimension of about 19 mm.

The discrete non-aperture zones of the present invention may be placed closer to each other, or they may be placed further apart from each other, provided that the overall area ratio of the discrete non-aperture zones over the nonwoven substrate remains within the desired range of from about 60% to about 90%. For example, the spacing between adjacent non-aperture zones may range from 1 mm to 1.5 mm, or from 1.2 mm to 1.6 mm, or from 1.4 mm to 1.6 mm.

In addition to the above-mentioned area ratios, areas and dimensions, the discrete non-aperture zones may further have an airy index, no less than about 270%, or no less than about 300%, or no less than about 350%, as measured according to Caliper Test. The discrete non-aperture zones may have a recovery airy index no less than about 160%, or no less than about 180%, or no less than about 200%, no less than about 220%, as measured according to Caliper Test. High airy index relates to an airy perception, both airy and recovery airy index link to a light touch cushiony feel.

Aperture Zones

The pattern formed by the apertures according to the present invention may also define one or more aperture zones, in addition to the discrete non-aperture zones disclosed hereinabove.

The aperture zone(s) of the present invention refer to the zone or area defined by a cluster of four or more apertures, while each aperture in said cluster has at least three (3) adjacent apertures that are spaced apart from it by an edge-to-edge distance (i.e., the shortest space between an edge of one aperture to an edge of an adjacent aperture, which is referred to hereinafter as "ED") of no more than about 3 mm.

Figure 3B:
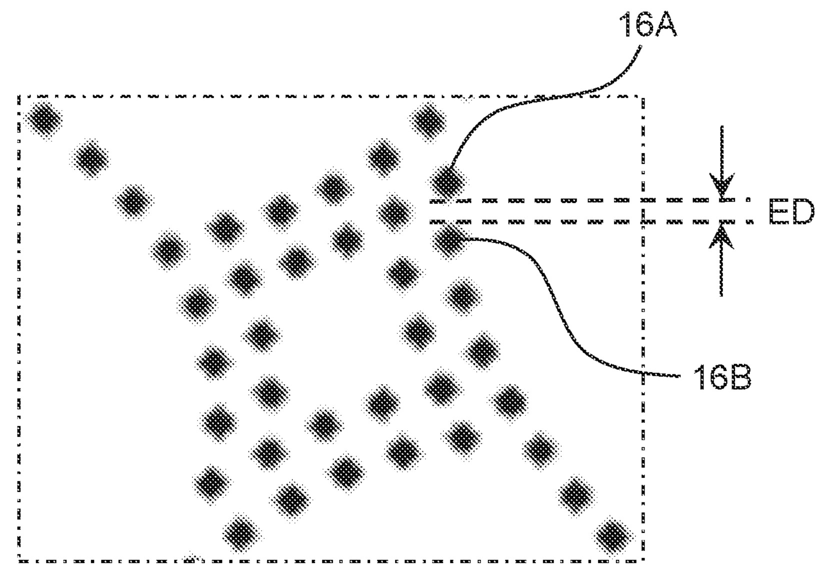
FIG. 3B is an enlarged schematic view of adjacent apertures in the apertured nonwoven substrate of FIG. 1.

For example, FIG. 3B shows two adjacent apertures 16A and 16B that are spaced apart from each other by an ED that is no more than 3 mm. Each of 16A and 16B has four (4) adjacent apertures that are spaced apart therefrom by an ED of no more than 3 mm. Other apertures in FIG. 3B also meet this criterion (i.e., having at least 3 adjacent apertures that are spaced apart from it by an ED of no more than 3 mm) and therefore belong to the same cluster as apertures 16A and 16B.

The nonwoven substrates of the present invention may comprise a plurality of discrete aperture zones, or a continuous aperture zone.

Figure 4:
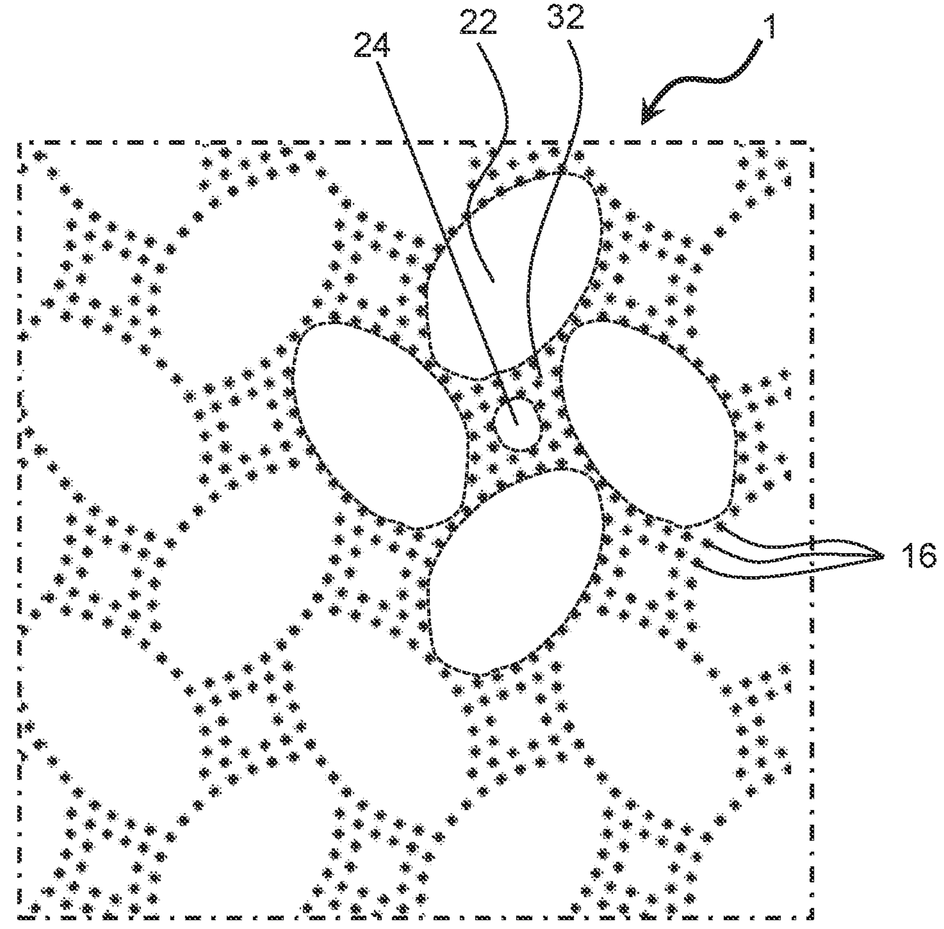
FIG. 4 is the top schematic view of the apertured nonwoven substrate of FIG. 1, with markings showing aperture zones.

FIG. 4 shows that aperture zone 32 (as defined by the above-mentioned clusters of adjacent apertures) is located adjacent to the plurality of discrete non-aperture zones 22 and 24 previously disclosed in FIG. 2.

Figure 5:
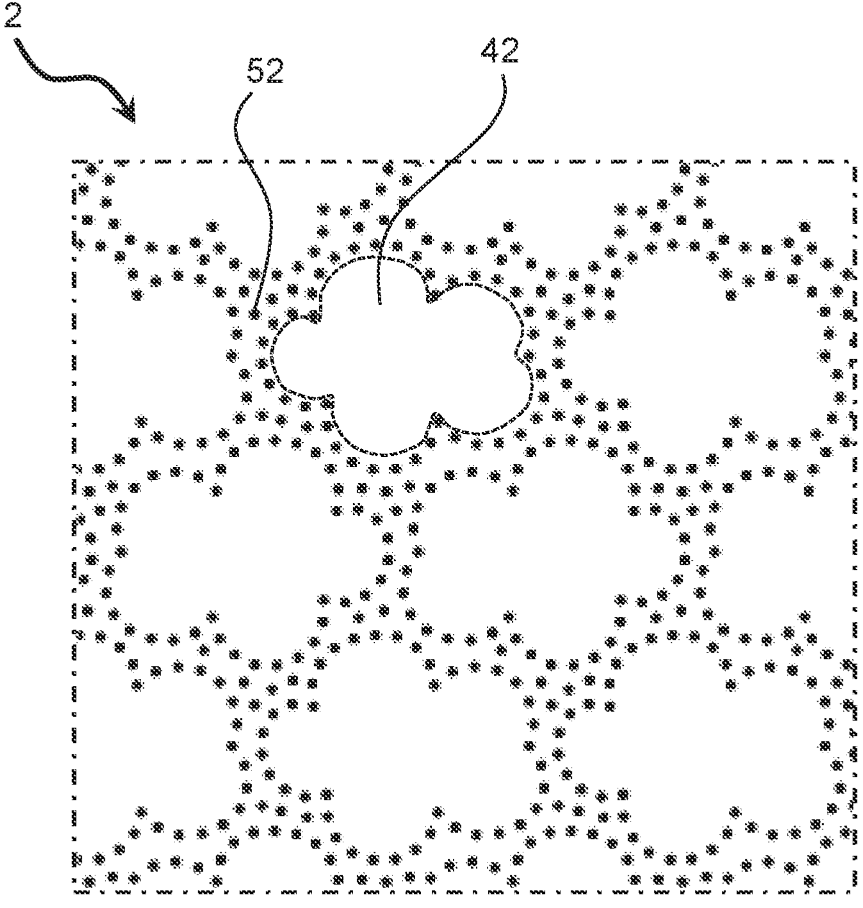
FIG. 5 is a top schematic view of another apertured nonwoven substrate, according to one embodiment of the present invention.

FIG. 5 shows another apertured nonwoven substrate 2 of the present invention. The nonwoven substrate 2 contains a plurality of cloud-shaped discrete non-aperture zones 42 of the same size, which are surrounded by aperture zone 52. The area ratio of the non-aperture zones 42 over the nonwoven substrate 2 (as measured from a 55 mm×55 mm sample of such nonwoven substrate) is about 66%, and each of the plurality of cloud-shaped discrete non-aperture zones 42 has an area of about 198 $mm^2$, so the apertured nonwoven substrate 2 falls within the scope of the present invention. Further, each of the plurality of cloud-shaped discrete non-aperture zones 42 has a major dimension of about 19 mm.

Figure 6:
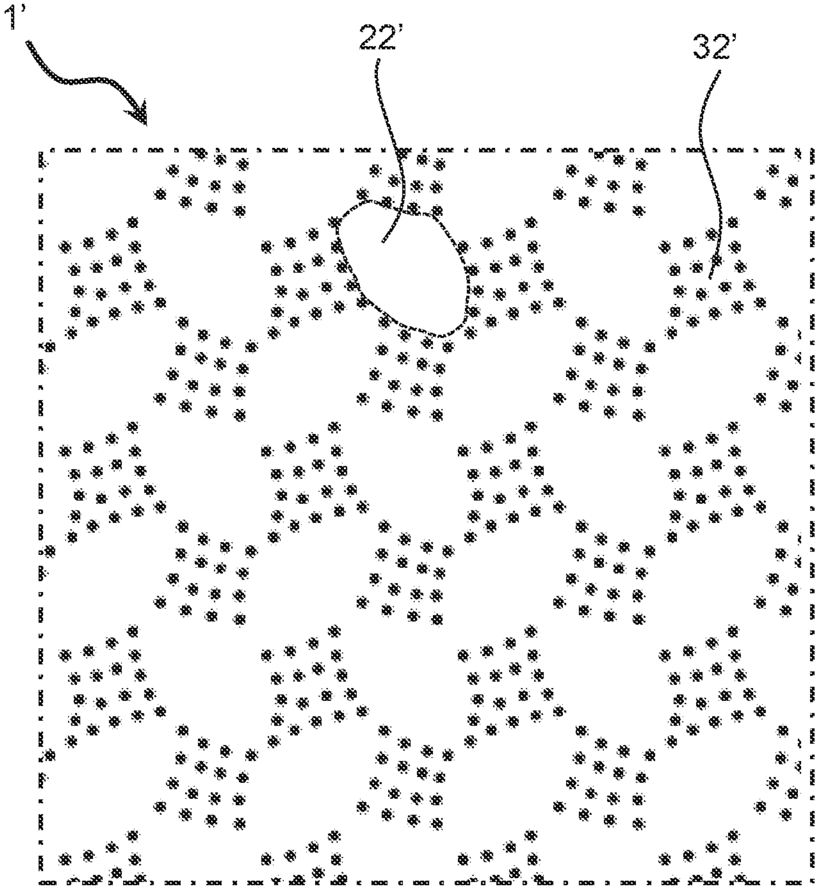
FIG. 6 is a top schematic view of a comparative apertured nonwoven substrate that does not fall within the scope of the present invention.
Figure 7:
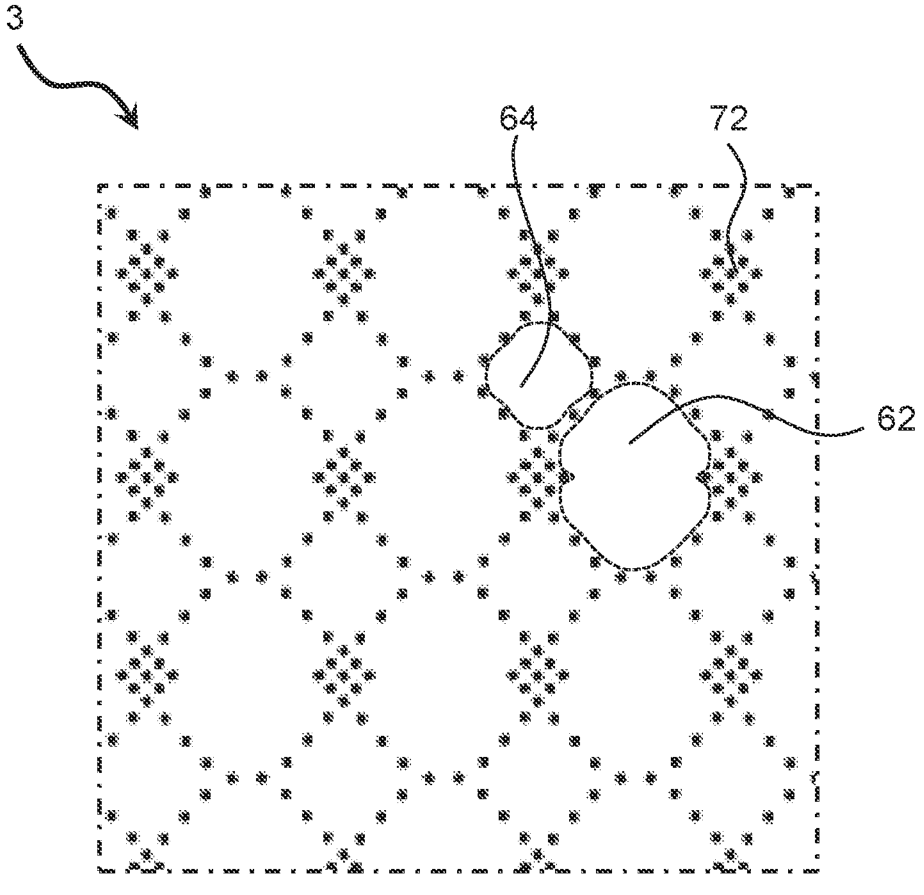
FIG. 7 is a top schematic view of another comparative apertured nonwoven substrate that does not fall within the scope of the present invention.

In contrast, FIGS. 6-7 show apertured nonwoven substrates that do not fall within the scope of the present invention.

Specifically, FIG. 6 shows an apertured nonwoven substrate 1' comprising a plurality of smaller leaf-shaped discrete non-aperture zones 22' adjacent to aperture zones 32'. Although the area ratio of the non-aperture zones 22' the nonwoven substrate 1' (as measured from a 55 mm×55 mm sample of such nonwoven substrate) is about 69% (within the desired area ratio range of from about 60% to about 90%), each of the smaller leaf-shaped discrete non-aperture zones 22' has an area of only about 78 $mm^2$ (below the desired area of 100 $mm^2$ or more) and a major dimension of about 13 mm (below the desired major dimension of 15 mm or more). The patterned and apertured nonwoven substrate of FIG. 6 is overall less appealing to or liked by the consumers, in comparison with those shown in FIGS. 1A and 5.

FIG. 7 shows an apertured nonwoven substrate 3 comprising a plurality of larger diamond-shaped non-aperture zones 62 and smaller diamond-shaped non-aperture zones 64 adjacent to a plurality of even smaller diamond-shaped aperture zones 72. However, such larger and smaller diamond-shaped non-aperture zones 62 and 64 are not discrete, because the majority or all of their peripheries are connected with or overlapping with the peripheries of one or more adjacent non-aperture zones. Therefore, the apertured nonwoven substrate 3 of FIG. 7 does not fall within the scope of the present invention. Correspondingly, the patterned and apertured nonwoven substrate of FIG. 7 is less appealing to or liked by the consumers overall, in comparison with those shown in FIGS. 1A and 5.

Other Structures

In addition to the above mentioned discrete non-aperture zones and aperture zones, the nonwoven substrate of the present invention may further a continuous non-aperture zone, or zones containing other three-dimensional structural elements (other than apertures), such as protrusions, recesses, turfs, ridges, grooves, embossing, and the like. The protrusion may have a higher caliper than the non-aperture zones.

In addition, the nonwoven substrate of the present invention may be characterized by more compressed and heat-fused fibers in the aperture zones in comparison with the non-aperture zones, which creates a capillarity difference. Specifically, the fluid travels from the non-aperture zones of a low capillarity to the aperture zones of a high capillarity due to the capillarity difference. As a result, the nonwoven substrate of the present invention can have a lower rewet amount and a smaller stain area when used as a topsheet of an absorbent article.

Absorbent Article

The present invention is directed to an absorbent article comprising a topsheet, a backsheet, an absorbent structure disposed between the topsheet and the backsheet, and the apertured nonwoven substrate of the present invention. In some embodiments, the absorbent article comprises a liquid pervious topsheet comprising the apertured nonwoven substrate of the preceding invention. In other embodiments, the absorbent article comprises a liquid impervious backsheet comprising the apertured nonwoven substrate of the preceding invention.

For example, the absorbent article of the present invention may be a sanitary napkin comprising a topsheet having a body-facing surface and a garment-facing surface positioned opposite to the body-facing surface. Said absorbent article may further comprise a backsheet having a garment-facing surface and a user-facing surface positioned oppositely to the garment facing surface. The backsheet is at least partially joined to the topsheet. The absorbent article may also comprise an absorbent core positioned between the topsheet and the backsheet. The absorbent article may further comprise a secondary topsheet and/or a pair of flaps or wings. The topsheet, the backsheet, and the absorbent core can be assembled in a variety of well-known configurations.

The backsheet and the topsheet can be secured together in a variety of ways. The topsheet and the backsheet can be joined to each other by using an adhesive, heat bonding, pressure bonding, ultrasonic bonding, dynamic mechanical bonding, or a crimp seal. A fluid impermeable crimp seal can resist lateral migration ("wicking") of fluid through the edges of the product, inhibiting side soiling of the user's undergarments.

When the absorbent article is a sanitary napkin, as is typical for sanitary napkins and the like, the sanitary napkin can have panty-fastening adhesive disposed on the garment facing side of backsheet. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the user's panties.

Topsheet

In the present application, a topsheet is the part of an absorbent article that is in contact with the user's skin. The topsheet may be joined to a backsheet, an absorbent core and/or any other layers as is known to those of skill in the art. Usually, the topsheet and the backsheet are joined directly to each other in some locations (e.g., on or close to the periphery of the absorbent article) and are indirectly joined together in other locations by directly joining them to one or more other components of the article.

The topsheet may be compliant, soft-feeling, and non-irritating to the user's skin. Further, a portion of, or all of, the topsheet may be liquid permeable, permitting liquids to readily penetrate through its caliper.

The topsheet comprises a nonwoven layer comprising a nonwoven substrate of the present disclosure. The topsheet can be a composite or a laminate comprising a nonwoven layer comprising a nonwoven substrate of the present disclosure. In any of various configurations, the nonwoven substrate of the present disclosure is intended to form at least a portion of the body facing surface of an absorbent article in such a way that apertures are towards in an absorbent core of the absorbent article.

The topsheet can also optionally include colorants, such as pigment, lake, toner, dye, ink or other agent used to impart a color to a material. Suitable pigments herein include inorganic pigments, pearlescent pigments, interference pigments, and the like.

Any portion of the topsheet may be coated with a lotion and/or a skin care composition as is generally disclosed in the art.

The topsheet may comprise an apertured nonwoven substrate of the present invention as descried hereinabove on its body-facing surface. The topsheet may also comprise a plurality of embossments to provide a more cloth like appearance.

The topsheet may be formed of any basis weight. However, relatively higher basis weight, while having relatively greater apparent caliper and loft, also has relatively greater cost. Suitable basis weight for the topsheet may be 200 gsm or less, or from 15 gsm to 80 gsm, or from 20 gsm to 70 gsm, or from 15 gsm to 60 gsm.

Absorbent Core

An absorbent core of an absorbent article serves to store bodily fluids discharged during use. The absorbent core can be manufactured in a wide variety of sizes and shapes, and may be profiled to have different caliper, hydrophilic gradients, superabsorbent gradients, densities, or average basis weights at different positions across the face of the product.

An absorbent core may comprise a fluid distribution layer as well as a fluid storage layer. The fluid distribution layer transfers received fluid both downwardly and laterally, and generally has more permeability and less capillarity than the fluid storage layer.

In addition to conventional absorbent materials such as creped cellulose wadding, fluffed cellulose fibers, wood pulp fibers also known as airfelt, and textile fibers, the fluid storage layer often includes superabsorbent material that imbibe fluids and form hydrogels. These materials are typically capable of absorbing large quantities of body fluids and retaining them under moderate pressures. The fluid storage layer of the absorbent core may comprise a superabsorbent material dispersed in a suitable carrier such as cellulose fibers in the form of fluff or stiffened fibers. The fluid storage layer of the absorbent core may comprise a superabsorbent material and be free from free cellulose fibers in the form of fluff or stiffened fibers.

Backsheet

The backsheet that covers the lower side of the absorbent core prevents the fluids in the absorbent core from wetting articles that contact the sanitary napkin, such as undergarments. Accordingly, the backsheet can be made from a liquid impervious thin film or a liquid impervious but vapor pervious film/nonwoven laminate, a microporous film, an apertured formed film, or other polymer film that is vapor permeable, or rendered to be vapor permeable, but substantially impervious to fluid.

The backsheet may comprise an apertured nonwoven substrate of the present invention as descried hereinabove on its user-facing surface, which will not affect the liquid impervious characteristic of such backsheet but will convey to the consumer a desired sense of breathability.

Apertured Nonwoven substrate Manufacturing Process

An apertured nonwoven substrate of the present invention may be manufactured by a method comprising the steps of providing a nonwoven substrate with a top surface and a bottom surface, and forming a plurality of apertures that each extends from the top surface through the nonwoven substrate to the bottom surface, while the plurality of apertures form a pattern according to the present invention as described hereinabove.

In one embodiment, the method for producing an apertured nonwoven substrate of the present invention comprises the steps of: supplying a nonwoven substrate unwound from a nonwoven roll, forming a plurality of apertures on the nonwoven substrate, and then applying heat to the nonwoven to restore bulkiness of the nonwoven.

An apertured nonwoven substrate of the present invention may be manufactured via a process comprising the steps of: supplying a nonwoven substrate unwound from a nonwoven roll, applying heat to the nonwoven to restore bulkiness of the nonwoven, and forming a plurality of apertures on the nonwoven substrate.

Aperture forming process may be conducted via various processes known to those skilled in the art such as aperturing process such as pin-hole aperturing, punch aperturing, and water-jet aperturing.

The apertured nonwoven of the present invention may be a relofted nonwoven. Relofting process is a process to make a nonwoven web regain its bulkiness by providing energy to the nonwoven web. Relofting process may be conducted via various processes known to those skilled in the art. A heating source includes oven, burner, or infrared radiation, producing heat to increase the temperature of the nonwoven substrate. As the temperature increases, fibers within the nonwoven substrate begin to soften, and at least some of the fibers begin to realign with, and/or detach from, the fibers. The realigning and/or detaching fibers cause the nonwoven substrate to increase in caliper, thereby decreasing the density of the nonwoven substrate. The final relofted caliper is dependent upon the temperature and the residence time, which is the overall time that the nonwoven substrate is exposed to the increased temperature in the relofting process.

In one embodiment, relofting a nonwoven can be conducted in accordance with methods disclosed in PCT/US2019/066455 filed on Sep. 5, 2019. The PCT application is hereby incorporated herein by reference in its entirety unless expressly excluded or otherwise limited. The method comprising: advancing a nonwoven substrate in a machine direction (MD), the nonwoven substrate comprising a first surface and an opposing second surface and defining a width in a cross direction; providing a first infrared radiation source; directing a first length of the nonwoven substrate to advance in a first direction such that the first surface of the first length of the nonwoven substrate is in a facing relationship with the first radiation source; and irradiating the first surface of the first length of the nonwoven substrate with infrared radiation from the first infrared radiation source, wherein the nonwoven substrate comprises a first caliper upstream of the first radiation source and wherein the nonwoven substrate comprises a second caliper downstream of the first radiation source, wherein the second caliper is higher than the first caliper.

so that the area of interest is located at the center of the sample holder and to be measured by the probe. The measuring probe moves down to the specimen and applies the forces in a normal direction following a method of stepwise compression (segments 1-10) and then stepwise recovery (segments 11-19) as specified below. The local caliper data of the specimen is collected in TMA at the same time with a frequency of 5 readings per second at regular intervals.

| Segment | 1 | 2 | 3 | 4 | 5 | 6 | 7 | 8 | 9 | 10 |
|---|---|---|---|---|---|---|---|---|---|---|
| Force (N) | 0.003 | 0.005 | 0.01 | 0.02 | 0.03 | 0.04 | 0.05 | 0.06 | 0.07 | 0.08 |
| Time (s) | 6 | 6 | 6 | 6 | 6 | 6 | 6 | 6 | 6 | 6 |

| Segment | 11 | 12 | 13 | 14 | 15 | 16 | 17 | 18 | 19 |
|---|---|---|---|---|---|---|---|---|---|
| Force (N) | 0.07 | 0.06 | 0.05 | 0.04 | 0.03 | 0.02 | 0.01 | 0.005 | 0.003 |
| Time (s) | 6 | 6 | 6 | 6 | 6 | 6 | 6 | 6 | 6 |

Aperture forming process and relofting process can be carried out consciously, or discontinuously.

Test Methods

1. Caliper Test

Thermomechanical Analysis (TMA), Module TMA/SDTA 1 IC/600, from Mettler-Toledo AG (Switzerland) or equivalent is used to measure the local caliper changes of nonwoven materials at ambient air condition as a function of the applied force. The measurements are conducted under the compression mode, using a quartz glass sample holder and a quartz glass measuring probe with flat circular end at the size of 3 mm in diameter.

If a nonwoven is available in its raw material form, a specimen with the dimensions of about 8 mm×5 mm is cut from the raw material. If a nonwoven is a component layer such as a topsheet of an absorbent article, a nonwoven specimen of this size is removed from the absorbent article, using a razor blade to excise the component layer from the underling layers of the absorbent article. A cryogenic spray (such as Cyto-Freeze, Control Company, Houston TX) or other suitable solvents that do not permanently alter the properties of the nonwoven specimen composition may be used to remove the topsheet specimen from the underling layers if necessary. For apertured nonwovens, specimens are sampled from different zones of the material, allowing the measurements on an apertured zone and a non-apertured zone separately.

Any remaining adhesive may be removed from the specimen by the following steps using Tetrahydrofuran (THF) as solvent.

1) In a hood, transfer 1 liter of THF into the 3-4 liter beaker.
2) Submerge specimen in the 1 liter of THF.
3) Place beaker on shaking table and stir gently for 15 minutes and keep solution with sample sit for 5 additional minutes.
4) Take specimen out of THE solution, and carefully squeeze THE solution out of specimen.
5) Let specimen air dry in hood for a minimum of 15 minutes.

Place a specimen flat at the sample holder with the consumer facing side exposed. Adjust the specimen position The specimen caliper measured at the midpoint (i.e. the time point of 3 s) of Segment 2 under the applied force of 0.005N or pressure of 0.1 psi is recorded as caliper at 0.1 psi. The specimen caliper measured at the midpoint of Segment 10 under the applied force of 0.08N or pressure of 1.6 psi is recorded as caliper at 1.6 psi. The specimen caliper measured during recovery at the midpoint of Segment 18 under the applied force of 0.005N or pressure of 0.1 psi is recorded as recovery caliper at 0.1 psi. Prepare and analyze a total of three substantially similar replicate samples for apertured and non-apertured zones respectively. The reported value is the arithmetic mean of the three replicate samples to the nearest integer in the unit of μm.

Caliper ratio at 0.1 psi is a caliper ratio between the non-apertured zone and the apertured zone measured at the pressure condition of 0.1 psi during compression. Airy Index and Recovery Airy Index are calculated using equations below.

$$\text{Airy Index }(\%) = [(\text{caliper at 0.1 psi} - \text{caliper at 1.6 psi})/\text{caliper at 1.6 psi}] \times 100$$

$$\text{Recovery Airy Index }(\%) = [(\text{recovery caliper at 0.1 psi} - \text{caliper at 1.6 psi})/\text{caliper at 1.6 psi}] \times 100$$

2. Compression Property Test

(1) Specimen Preparation

To obtain a nonwoven raw material specimen, lay the material flat on a bench with the technical face-side upward, and a 110 mm×110 mm square shape of specimen are cut using scissors. The technical face-side is the surface intended to be used as the body facing surface when the nonwoven is used as a component in an absorbent article.

To obtain a specimen of a topsheet nonwoven from an absorbent article, a 110 mm×110 mm topsheet specimen is removed from the absorbent article, centered at the intersection of the longitudinal and lateral centerlines of the absorbent article. For the purpose of removing the topsheet from the absorbent article, a razor blade is used to excise the topsheet from the underling layers of the absorbent article around the outer perimeter for the area of 110 mm×110 mm. A cryogenic spray (such as Cyto-Freeze, Control Company, Houston TX) may be used to remove the topsheet specimen from the underling layers if necessary. The specimen needs to be conditioned for at least 4 hours in a room maintained at 23±2° C. and 50±5% relative humidity before testing.

(2) Compression Work

Compression work denotes the total work done on the specimen during the compression process. Integral of the compression curve according to equation (1) is obtained wherein Da is the initial caliper at zero pressure, De is minimum caliper at maximum pressure, F is the measured force and D is the measured caliper during compression.

$$CW = \int_{D_a}^{D_c} F dD \quad (1)$$

Compression work of specimens are measured using the Fabric Touch Tester (FTT M293) running FTT system software (available from SDL Atlas), or equivalent. FTT includes five modules, which may be activated at the same time and recorded of the dynamic responses from the specimens, depending on the specimen. They include compression, thermal, bending, friction, and surface modules. The instrument is calibrated according to the manufacturer's instructions using the standard calibration fabric provided by the vendor. All testing is performed in a room maintained at 23±2° C. and 50±5% relative humidity. The test procedures are conducted according to the Operating Instructions for the FTT M293 manual.

The 110 mm×110 mm specimen with technical face-side upward is placed centrally on the lower plate. The Compression test is initiated with single surface testing mode and the specimen would be pushed downwards by the upper plate applying a continuously increasing normal force from 0-8470 gf (i.e. 0-70 gf/cm$^2$).

Five specimens are measured, and compression work, or any subset thereof, are calculated and reported with the average value.

3. Non-Aperture Zone Area/Size and Area Ratio Measurement (A) Sample Preparation When a nonwoven is available in a raw material form, a specimen with a size of 55 mm×55 mm is cut from the raw material. When a nonwoven is a component of a finished product, the nonwoven is removed from the finished product using a razor blade to excise the nonwoven from other components of the finished product to provide a nonwoven specimen with a size of 55 mm×55 mm. A cryogenic spray (such as Cyto-Freeze, Control Company, Houston TX) may be used to remove the nonwoven specimen from other components of the finished product, if necessary.

(B) Image Generation

The nonwoven specimen is placed flat against a dark background under uniform surface lighting conditions. The entire area of the specimen is scanned using an optical microscope such as Keyence 3D Measurement System VR-3200 or equivalent. The analysis such as area ratio measurement is performed using image analysis program such as ImageJ software (version 1.52p or above, National Institutes of Health, USA) and equivalent. The images need to be distance calibrated with an image of a ruler to give an image resolution. Set the scale according to the image resolution and select the field of view size of 55 mm×55 mm for the nonwoven specimen.

(C) Image Analysis—Make a Binary Image

Open a specimen image in ImageJ. Convert the image type to 8 bits. The 8-bit grayscale image is then converted to a binary image (with "black" foreground pixels corresponding to the apertures) using the "Minimum" thresholding method: If the histogram of gray level (GL) values (ranging from 0 to 255, one bin with propensity $P_i$ per gray level i) has exactly two local maxima, the threshold gray level value t is defined as that value for which $P_{t-1}>P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1}>P_t$ and $P_t \leq P_{t+1}$. This procedure identifies the gray level (GL) value for the minimum population located between the dark pixel peak of apertures and the lighter pixel peak of the specimen material. If the histogram contains either zero or one local maximum, the method cannot proceed further, and no output parameters are defined.

(D) Size/Area and Area Ratio of Discrete Non-Aperture Zones

Create a filtered image by removing small openings or defects in the binary image using an outlier removing median filter, which replaces a pixel with median of the surrounding area of e.g. 5 pixels in radius if the pixel is darker than the surrounding. Create a reversed image so that discreate non-aperture zones have pixel values of 255.

An ImageJ plugin "Local Thickness" is applied to the image. The local thickness analysis measures the diameter of the largest sphere that fits inside the object and contains the point for each point, i.e., foreground pixel in an image. (reference: "New algorithms for Euclidean distance transformation on an n-dimensional digitized picture with applications", T. Saito and J. Toriwaki, Pattern Recognition 27, 1994, 1551-1565). Convert the image type of local thickness map to 16 bits.

An ImageJ plugin "k-means Clustering" is applied to the image obtained above, which segments the image in the defined number of clusters with similar intensity. The options for k-means clustering used in this analysis are: 5 clusters (i.e., 5 segments image will be divided into); cluster center tolerance of 0.0001; enable randomization seed (randomization seed: 48); show clusters as centroid value. Use the image of clusters represented by centroid value and segment it via centroid value thresholding to only select the discrete non-aperture zones. The histogram data of the binary image is used to calculate the area ratio (%) of discrete non-aperture zones by dividing the counts of foreground pixels (corresponding to the discrete non-aperture zones) with the total pixel counts of the entire area of the image, and multiplying it by 100%. The value is reported to the nearest 1%. The same image is also used for the size/area analysis. Set the scale according to the image resolution. Use watershed segmentation if necessary to separate the discrete non-aperture zones that touch each other. Measure the area (mm$^2$) of each of the discrete non-aperture zones, when excluding the incomplete ones on the edge of the image. The size/area of discrete non-aperture zones is the arithmetic mean of the area values and reported to the nearest 1 mm$^2$.

(E) Consumer Test for Measuring Perceived Overall Liking (OAR)

To understand consumer's overall preference on different apertured pattern designs on sanitary napkins ("Samples"), 26 female panelists who have menstruated in past 3 months (age 18-40) are recruited. Samples with topsheets formed by patterned and apertured nonwovens of different aperture pattern designs are shown to these panelists. They are asked to rate the Samples in 1-10 scale for overall liking (OAR) of the products (Score "1" means extremely disliking, score "6" means acceptable, score "10" means extremely liking). Then the average OAR score of each Sample is calculated and reported with the standard deviation value.

(F) Consumer Test for Measuring Premiumness, Breathability, Absorbency, Softness, Distinctiveness, and/or 3Dness To understand consumer's preference on different apertured pattern designs on sanitary napkins with respective to specific product attributes, 30 female panelists who have menstruated in past 3 months (age 18-40) are recruited. Product-rendering images with topsheets containing patterned and apertured nonwovens of different aperture pattern designs ("Sample Images") are showed to the consumers who are then asked to rate the Sample Images in 1-10 scale for: (1) Premiumness, (2) Breathability, (3) Absorbency, (4) Softness, (5) Distinctiveness, and/or (6) 3Dness of the products (Score "1" means poor, score "6" means acceptable, score "10" means excellent). The average score of the specific product attribute of interest (i.e., Premiumness, Breathability, Absorbency, Softness, Distinctiveness, and/or 3Dness) for each Sample Image is then calculated and reported with the standard deviation value.

EXAMPLES

Example 1. Comparative Test Showing Consumer Overall Liking of Apertured Nonwovens with Different Patterns Nonwoven Samples A-D with patterned apertures as shown in FIGS. 2 and 5-7 are first provided and then used for testing the overall consumer liking of them. These Samples are carded air-through nonwovens made from a top layer of 2 denier PET/PE core/sheath bicopolymer fibers and a bottom layer of 2 denier PP/PE core/sheath bicopolymer fibers via a conventional carding process.

The area ratios and dimensions of the discrete non-aperture zones in such apertured nonwoven Samples A-D are calculated and tableted together with their respective OAR test results (as measured by Test 4), as follows:

TABLE 1

| | Inventive | | Comparative | |
|---|---|---|---|---|
| Patterns | A<br>Big Leaf<br>(FIG. 2) | B<br>Cloud<br>(FIG. 5) | C<br>Small Leaf<br>(FIG. 6) | D<br>Diamond<br>(FIG. 7) |
| Area Ratio* | 75% | 66% | 69% | N/A |
| Area/Size** | 189 $mm^2$ | 198 $mm^2$ | 78 $mm^2$ | N/A |
| Major Dimension** | 19 mm | 19 mm | 13 mm | N/A |
| OAR*** | 7.65 ± 1.35 | 7.73 ± 1.82 | 6.96 ± 1.11 | 6.62 ± 1.55 |

*The area ratio of discrete non-aperture zones over the nonwoven substrate, as measured by Test Method 3.

**That of each of the largest discrete non-aperture zones in the respective nonwoven substrate, as measured by Test Method 3.

***There is a significant difference between the OAR scores of Inventive Samples A and B and that of Comparative Sample D (significance calculated at a 85% confidence interval), and the OAR scores of Inventive Samples A and B are directionally better than that of Comparative Sample C.

It is clear from the above data that the inventive nonwoven substrates A and B according to the present invention are overall more preferred/liked by consumers than the comparative nonwoven substrates C and D that do not fall within the scope of the present invention.

Example 2. Comparative Test Showing Impact of Aperture Sizes on Consumer-Perceived Premiumness of Apertured Nonwovens with Similar Patterns FIG. 8 shows multiple apertured nonwoven substrates of the present invention, with similar patterns ("Big Leaf") formed by apertures of different sizes (e.g., with diameters ranging from 0.5 mm to 1.4 mm and areas ranging from 0.2 $mm^2$ to 1.5 $mm^2$).

Figure 8:
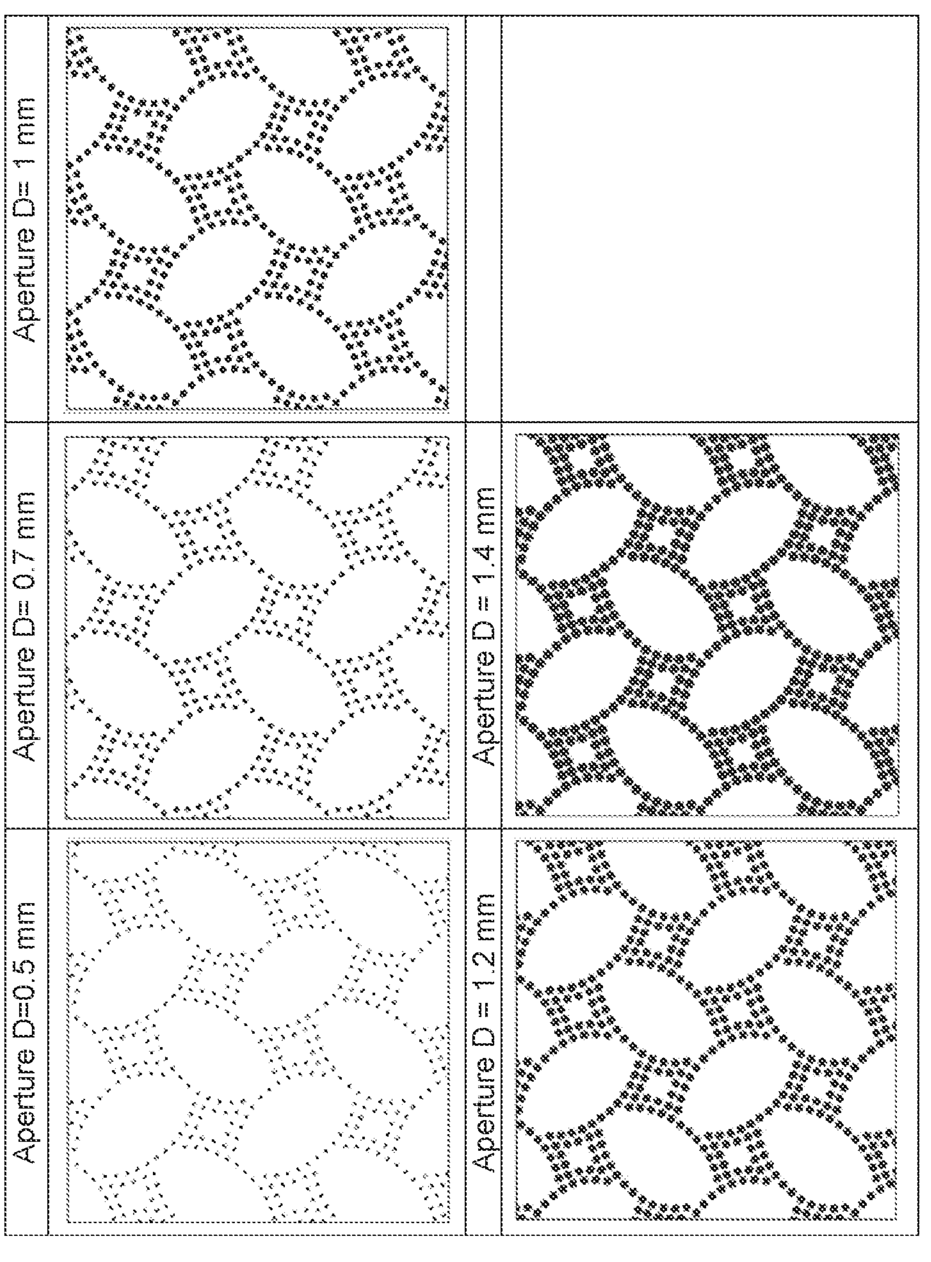
FIG. 8 shows the top schematic views of multiple apertured nonwoven substrates having similar patterns formed by apertures of different sizes, according to one embodiment of the present invention.

Photorealistic digital images showing sanitary napkins with topsheets made of apertured nonwoven substrates with patterned apertured designs as shown in FIG. 8 are generated using the methodologies of digitally synthesizing visual content well known in the art of computer graphics and 3D rendering. Specifically, a high-resolution 3D model of sanitary napkin product is first developed using polygonal modeling process or other ways to provide the geometry information. A rendering plug-in of V-Ray for Autodesk **3*ds*** Max or equivalent 3D computer graphics software is used to apply a ray-tracing algorithm for producing images with more photorealism, by tracing the path of light through each pixel in an image plane and simulating the effects of its encounters with virtual objects. Multiple layers of materials with preferred rendering parameters, representing the product components such as topsheet nonwoven material are superposed and virtually mixed to generate the prototyping results. The changes in visual attributes comprising 2D/3D surface texture design (e.g. patterns of apertures or protrusions) and material optical properties such as reflection and opacity are implemented and visualized through rendering in an effective way.

Such images are then used for testing the consumer perceived Premiumness of the sample products.

The area ratios of the discrete non-aperture zones in the above-described apertured nonwovens are calculated and then tableted together with their respective Premiumness test results (as measured by Test 5), as follows:

TABLE 2

| Aperture Diameter | D = 0.5 mm | D = 0.7 mm | D = 1 mm | D = 1.2 mm | D = 1.4 mm |
|---|---|---|---|---|---|
| Aperture Area | A = 0.2 mm$^2$ | A = 0.4 mm$^2$ | A = 0.8 mm$^2$ | A = 1.3 mm$^2$ | A = 1.5 mm$^2$ |
| Area Ratio* | 78% | 75% | 72% | 69% | 67% |
| Premiumness** | 6.5 ± 1.0 | 7.1 ± 1.1 | 7.1 ± 1.3 | 7.0 ± 1.4 | 7.0 ± 1.5 |

*The area ratio of the discrete non-aperture zones over the nonwoven substrate, as measured by Test Method 3.

**There is a significant difference between the premiumness scores of the nonwoven substrates containing apertures with diameters of 0.5 mm and 0.7 mm (significance calculated at a 85% confidence interval), and the premiumness scores of the nonwoven substrates containing apertures with diameters of 0.7/1/1.2/1.4 mm are directionally better than that of 0.5 mm.

The above data shows that the nonwoven substrates having apertures of the appropriate sizes (e.g., 0.7 mm or 1 mm) may convey to the consumers an improved sense of premiumness, in comparison with nonwoven substrates having smaller or larger apertures.

Example 3. Comparative Test Showing Impact of Aperture Density on Consumer-Perceived Premiumness of Apertured Nonwovens with Similar Patterns FIG. 9 shows multiple apertured nonwoven substrates having similar patterns ("Cloud"), with discrete non-aperture zones of the same shapes/sizes but with apertures of different densities (i.e., the spacings between adjacent apertures within the aperture zones are different), according to one embodiment of the present invention.

Figure 9:
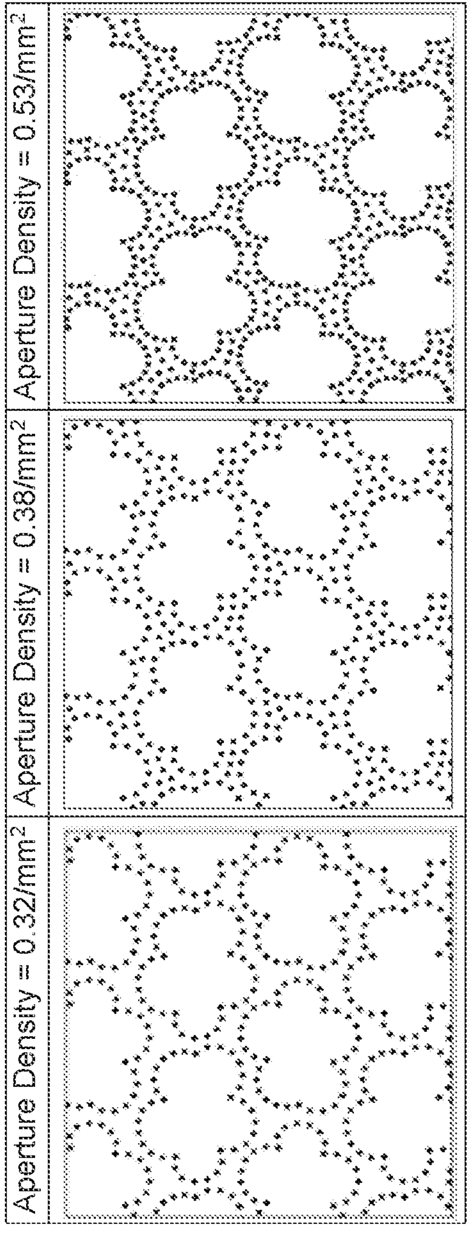
FIG. 9 shows the top schematic views of multiple apertured nonwoven substrates having similar patterns formed by apertures of different density, according to one embodiment of the present invention.

Photorealistic digital images showing sanitary napkins with topsheets made of apertured nonwoven substrates with patterned apertured designs as shown in FIG. 9 are generated using the same methodologies as described in Example 2. Such images are then used for testing the consumer perceived Premiumness of the sample products.

The aperture density and the area ratios of the discrete non-aperture zones in the above-described apertured nonwovens are calculated and then tableted together with their respective Premiumness test results (as measured by Test 5), as follows:

TABLE 3

| Aperture Density (1/mm$^2$)* | 0.32 | 0.38 | 0.53 |
|---|---|---|---|
| Area Ratio** | 65% | 65% | 65% |
| Premiumness*** | 6.9 ± 1.1 | 7.1 ± 1.3 | 7.3 ± 1.2 |

*The average number of apertures within 1 mm$^2$ of the aperture zones, which is calculated as the total # of apertures divided by the total area of the aperture zones.

**The area ratio of the discrete non-aperture zones over the nonwoven substrate, as measured by Test Method 3.

***The premiumness score of the nonwoven substrates containing apertures with aperture densities of 0.53/mm$^2$ is directionally better than that of 0.32/mm$^2$.

The above data shows that the nonwoven substrates having discrete non-aperture zones of the same shape/sizes (and correspondingly similar area ratios) but with significantly higher aperture densities convey to the consumers an improved sense of premiumness.

Example 4. Comparative Test Showing Impact of Spacings Between Discrete Non-Aperture Zones on Consumer-Perceived Premiumness of Apertured Nonwovens with Similar Patterns FIG. 10 shows multiple apertured nonwoven substrates having similar patterns ("Cloud"), with discrete non-aperture zones of the same shapes/sizes but with different spacings therebetween ("NAZ Distance"), according to one embodiment of the present invention.

Figure 10:
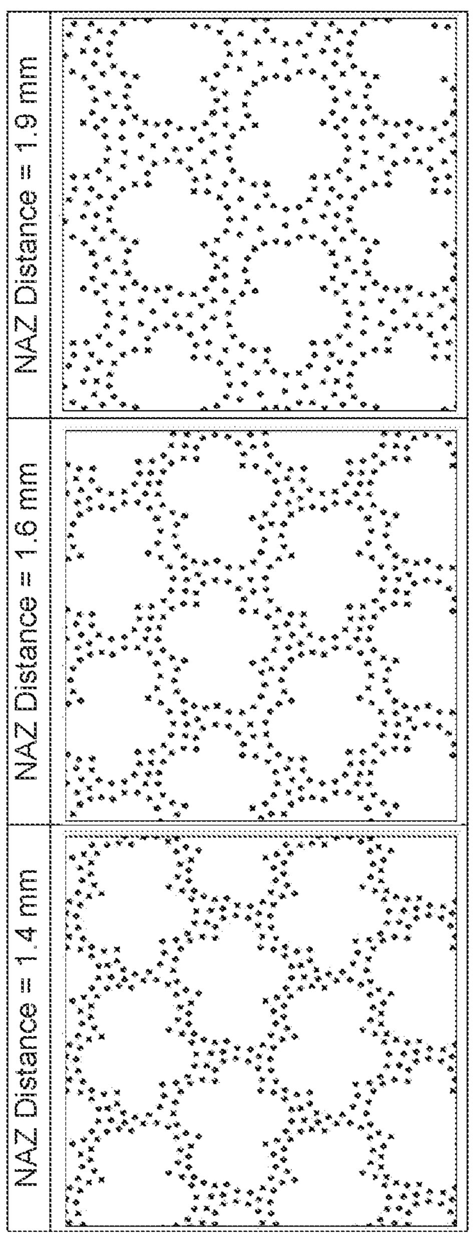
FIG. 10 shows the top schematic views of multiple apertured nonwoven substrates having similar patterns and comprising discrete non-aperture zones with different spacings therebetween, according to one embodiment of the present invention.

Photorealistic digital images showing sanitary napkins with topsheets made of apertured nonwoven substrates with patterned apertured designs as shown in FIG. 10 are generated using the same methodologies as described in Example 2. Such images are then used for testing the consumer perceived Premiumness of the sample products.

The NAZ distances and the area ratios of the discrete non-aperture zones in the above-described apertured nonwovens as shown in FIG. 10 are calculated and then tableted together with their respective Premiumness test results (as measured by Test 5), as follows:

TABLE 4

| NAZ Distance* (mm) | 1.4 | 1.6 | 1.9 |
|---|---|---|---|
| Area Ratio** | 73% | 66% | 51% |
| Premiumness*** | 7.2 ± 1.2 | 7.2 ± 1.1 | 6.8 ± 1.2 |

*That between adjacent discrete non-aperture zones in the respective nonwoven substrate, which is calculated as the total aperture zone area divided by the number of apertures, and then calculating the square root thereof.

**The area ratio of the discrete non-aperture zones over the nonwoven substrate, as measured by Test Method 3.

***The premiumness scores of nonwoven substrates with 1.4 mm and 1.6 mm spacing between non-aperture zones are directionally better than that with 1.9 mm spacing.

The above data shows that the nonwoven substrates having discrete non-aperture zones of the same shape/sizes but with less spacing therebetween (i.e., the left and middle nonwoven substrates in FIG. 10) convey to the consumers a better sense of premiumness, in comparison with that having more spacing (i.e., the right nonwoven substrate in FIG. 10). Note that as the spacing between adjacent discrete non-aperture zones increases, the area ratio of the discrete non-aperture zones over the nonwoven substrate also reduces, e.g., to below the desired range (i.e., below 60%), which may contribute to a reduced premiumness perceived by the consumers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven substrate comprising:

a) a top surface;

b) a bottom surface; and c) a plurality of apertures, each of which extends from the top surface through said nonwoven substrate to the bottom surface, wherein said plurality of apertures define a plurality of discrete non-aperture zones; wherein each of said plurality of discrete non-aperture zones has a periphery formed by a continuous line of apertures; wherein each of said plurality of discrete non-aperture zones is substantially free of apertures within the periphery; wherein the area ratio of said plurality of discrete non-aperture zones over said nonwoven substrate ranges from 60% to 90%; and wherein some of said plurality of discrete non-aperture zones have an area of 100 $mm^2$ or more, wherein each of said plurality of apertures has a size of greater than about 0.2 $mm^2$, and wherein said plurality of apertures further define one or more aperture zones; wherein each of said one or more aperture zones comprises four or more apertures therein; wherein each aperture within each of said aperture zones has at least three adjacent apertures.

2. The nonwoven substrate of claim 1, wherein the area ratio of said plurality of discrete non-aperture zones over said nonwoven substrate ranges from 62% to 80%, or from 65% to 75%.

3. The nonwoven substrate of claim 1, wherein some of said plurality of discrete non-aperture zones have an area of 150 $mm^2$ or more, or 200 $mm^2$ or more, or 300 $mm^2$ or more.

4. The nonwoven substrate of claim 1 wherein each of said plurality of apertures has a diameter ranging from 0.5 mm to 1.5 mm, or from 0.7 mm to 1.2 mm; and/or wherein said plurality of apertures have regular shapes selected from the group consisting of circle, oval, triangle, square, rectangle, parallelogram, trapezoid, polygon, hour-glass, star, and any combinations thereof.

5. The nonwoven substrate of claim 1, wherein each of said plurality of discrete non-aperture zones has an area of more than 6 $mm^2$; and/or wherein each of said plurality of discrete non-aperture has a minor dimension of more than 2.5 mm.

6. The nonwoven substrate of claim 1, wherein some of said plurality of discrete non-aperture zones have a major dimension of 15 mm or more, or 18 mm or more, or 20 mm or more.

7. The nonwoven substrate of claim 6, comprising a plurality of discrete aperture zones.

8. The nonwoven substrate of claim 6, comprising a continuous aperture zone.

9. The nonwoven substrate of claim 1, wherein the nonwoven substrate is a relofted nonwoven.

10. The nonwoven substrate of claim 1, wherein the nonwoven substrate has:

a compression work no less than about 700 gf×mm, as measured according to Compression Property Test; and/or a basis weight in the range of about 15 gsm to about 75 gsm.

11. An absorbent article comprising a liquid pervious topsheet, a liquid impervious backsheet, an absorbent structure disposed between the topsheet and the backsheet, wherein the liquid pervious topsheet comprises the nonwoven substrate according to claim 1.

12. An absorbent article comprising a liquid pervious topsheet, a liquid impervious backsheet, an absorbent structure disposed between the topsheet and the backsheet, wherein the liquid impervious backsheet comprises the nonwoven substrate according to claim 1.

13. A method for manufacturing an apertured nonwoven substrate, comprising the steps of:

providing a nonwoven substrate having a top surface and a bottom surface; and forming a plurality of apertures that each extends from the top surface through said nonwoven substrate to the bottom surface, wherein said plurality of apertures define a plurality of discrete non-aperture zones; wherein each of said plurality of discrete non-aperture zones has a periphery formed by a continuous line of apertures; wherein each of said plurality of discrete non-aperture zones is substantially free of apertures within the periphery; wherein the area ratio of said plurality of discrete non-aperture zones over said nonwoven substrate ranges from 60% to 90%; and wherein some of said plurality of discrete non-aperture zones have an area of 100 $mm^2$ or more, wherein each of said plurality of apertures has a size greater than about 0.2 $mm^2$, and wherein said plurality of apertures further define one or more aperture zones; wherein each of said one or more aperture zones comprises four or more apertures therein; wherein each aperture within each of said aperture zones has at least three adjacent apertures.

14. A nonwoven substrate comprising:

a) a top surface;

b) a bottom surface; and c) a plurality of apertures, each of which extends from the top surface through said nonwoven substrate to the bottom surface, wherein said plurality of apertures define a plurality of discrete non-aperture zones; wherein each of said plurality of discrete non-aperture zones has a periphery formed by a continuous line of apertures; wherein each of said plurality of discrete non-aperture zones is substantially free of apertures within the periphery; wherein the area ratio of said plurality of discrete non-aperture zones over said nonwoven substrate ranges from 60% to 90%; and wherein some of said plurality of discrete non-aperture zones have an area of 100 $mm^2$ or more, wherein each of said plurality of discrete non-aperture zones has an area of more than 6 $mm^2$, wherein each of said plurality of discrete non-aperture has a minor dimension of more than 2.5 mm, and wherein said plurality of apertures further define one or more aperture zones; wherein each of said one or more aperture zones comprises four or more apertures therein.

15. An absorbent article comprising a liquid pervious topsheet, a liquid impervious backsheet, an absorbent structure disposed between the topsheet and the backsheet, wherein the liquid pervious topsheet comprises the nonwoven substrate according to claim 14.

16. The nonwoven substrate of claim 14, wherein the substrate has a basis weight of about 15 gsm to about 75 gsm.

17. The nonwoven substrate of claim 14, wherein some of said plurality of discrete non-aperture zones have a major dimension of greater than 15 mm.

18. The nonwoven substrate of claim 14, wherein each of said plurality of apertures has a diameter ranging from 0.5 mm to 1.5 mm.

19. The nonwoven substrate of claim 14, wherein a portion of said plurality of discrete non-aperture zones have an area of greater than about 150 $mm^2$.

20. An absorbent article comprising a liquid pervious topsheet, a liquid impervious backsheet, an absorbent structure disposed between the topsheet and the backsheet, wherein the liquid impervious backsheet comprises the nonwoven substrate according to claim 14.

* * * * *